US006568387B2

(12) United States Patent
Davenport et al.

(10) Patent No.: US 6,568,387 B2
(45) Date of Patent: May 27, 2003

(54) METHOD FOR TREATING CHRONIC OBSTRUCTIVE PULMONARY DISORDER

(75) Inventors: Paul W. Davenport, Gainesville, FL (US); Anatole D. Martin, Gainesville, FL (US)

(73) Assignee: University of Florida, Gainesville, FL (US)

( * ) Notice: Subject to any disclaimer, the term of this patent is extended or adjusted under 35 U.S.C. 154(b) by 85 days.

(21) Appl. No.: 09/908,329

(22) Filed: Jul. 18, 2001

(65) Prior Publication Data

US 2002/0007831 A1 Jan. 24, 2002

Related U.S. Application Data

(60) Provisional application No. 60/219,307, filed on Jul. 19, 2000.

(51) Int. Cl.$^7$ ............... A61M 15/00; A61M 16/00; A62B 18/00; A62B 7/00; A62B 9/00
(52) U.S. Cl. ................. 128/200.24; 128/204.18; 428/13
(58) Field of Search ............. 128/200.24, 204.18, 128/204.23, 205.24, 205.25, 203.11, 207.12, 207.16; 600/529, 533, 538; 482/13

(56) References Cited

U.S. PATENT DOCUMENTS

| 4,182,366 | A | | 1/1980 | Boehringer | |
|---|---|---|---|---|---|
| 4,207,884 | A | | 6/1980 | Isaacson | |
| 4,345,593 | A | | 8/1982 | Sullivan | |
| 4,354,520 | A | * | 10/1982 | Easley, Jr. ............ | 137/543.23 |
| 4,403,616 | A | | 9/1983 | King | |
| 4,533,137 | A | | 8/1985 | Sonne | |
| 4,601,465 | A | | 7/1986 | Roy | |
| 4,625,759 | A | * | 12/1986 | Craig .................... | 137/613 |
| 4,640,293 | A | * | 2/1987 | Garbe .................... | 600/529 |
| 4,655,213 | A | * | 4/1987 | Rapoport et al. ...... | 128/205.25 |
| 4,739,987 | A | | 4/1988 | Nicholson | |
| 4,773,411 | A | | 9/1988 | Downs | |
| 4,854,574 | A | | 8/1989 | Larson et al. | |
| 4,870,963 | A | | 10/1989 | Carter | |
| 4,973,047 | A | | 11/1990 | Norell | |
| 4,981,295 | A | | 1/1991 | Belman et al. | |
| 5,059,208 | A | * | 10/1991 | Coe et al. ............ | 623/9 |
| 5,067,707 | A | | 11/1991 | Kohnke | |
| 5,109,840 | A | | 5/1992 | Daleiden | |
| 5,123,922 | A | * | 6/1992 | Berg .................... | 623/9 |
| 5,161,525 | A | * | 11/1992 | Kimm et al. ......... | 128/204.26 |
| 5,451,190 | A | | 9/1995 | Liardet | |
| 5,598,839 | A | | 2/1997 | Niles et al. | |
| 5,649,533 | A | | 7/1997 | Oren | |
| 5,660,171 | A | * | 8/1997 | Kimm et al. ......... | 128/204.23 |
| 5,685,296 | A | * | 11/1997 | Zdrojkowski et al. . | 128/205.24 |
| 5,701,885 | A | * | 12/1997 | Hale .................... | 128/201.26 |
| 5,730,122 | A | * | 3/1998 | Lurie .................... | 128/207.12 |
| 5,878,743 | A | | 3/1999 | Zdrojkowski et al. | |
| 5,899,832 | A | | 5/1999 | Hougen | |
| 5,915,381 | A | | 6/1999 | Nord | |
| 5,937,855 | A | * | 8/1999 | Zdrojkowski et al. . | 128/205.24 |
| 5,937,857 | A | * | 8/1999 | Caterini et al. ........ | 128/207.12 |
| 6,029,667 | A | * | 2/2000 | Lurie .................... | 128/207.16 |
| 6,105,575 | A | | 8/2000 | Estes et al. | |
| 6,165,105 | A | | 12/2000 | Boutellier et al. | |
| 6,439,233 | B1 | * | 8/2002 | Geertsema ............ | 128/207.16 |
| 6,470,888 | B1 | * | 10/2002 | Matter .................... | 128/207.14 |
| 6,484,723 | B2 | * | 11/2002 | Haas .................... | 128/207.14 |

* cited by examiner

*Primary Examiner*—Weilun Lo
*Assistant Examiner*—Joseph F. Weiss, Jr.
(74) *Attorney, Agent, or Firm*—Saliwanchik, Lloyd & Saliwanchik

(57) ABSTRACT

The present invention relates generally to the field of breathing exercise devices and more particularly to expiratory breathing methods which promote proper resistance breathing by the user. More specifically, the present invention discloses a method which utilizes a pressure relief valve, preferably a positive end-expiratory pressure (PEEP) valve, for providing positive expiratory pressure (PEP). The PEP is provided by obstructing the flow of gases exhaled by the patient through the PEEP valve, so that such gases must be exhaled against the PEEP valve's pressure threshold.

31 Claims, 3 Drawing Sheets

METHOD FOR TREATING CHRONIC OBSTRUCTIVE PULMONARY DISORDER

CROSS-REFERENCE TO A RELATED APPLICATION

This application claims the benefit of U.S. Provisional Application No. 60/219,307, filed Jul. 19, 2000, incorporated herein by reference.

FIELD OF INVENTION

The present invention relates generally to the field of breathing exercise and more particularly to an expiratory breathing method which promotes proper pressure breathing by the user.

BACKGROUND INFORMATION

Dynamic airway collapse during expiration is a major problem in patients with chronic obstructive airways disease (COPD). Dynamic airway compression) and/or collapse) is the reason why forced expiratory efforts are effort independent. The movement of air out of the lung requires a positive pressure driving force that is greater in the alveoli than at the mouth. This creates a pressure gradient in which air will move down by bulk flow.

There are two sources of positive pressure during expiration: 1) the recoil pressure generated by the elasticity of the lung, and 2) active compression of the lung with contraction of the expiratory muscles. The lung has an elasticity that is measured as compliance. An analogy is a balloon. When the balloon is inflated, the latex is stretched from its rest position. Holding the end of an inflated balloon closed one can feel the positive pressure inside the balloon as the latex squeezes the air in the balloon attempting to return to its rest position. If the balloon end is opened, air will flow out of the balloon because of the pressure gradient generated by the elastic recoil of the balloon wall.

The lung has elasticity and when the lung is inflated with a large inspiration, the lung walls are stretched. The lung elastic tissue will compress the air in the lung creating a positive pressure that is proportional to the lung stretch, the lung volume. Active contraction of the expiratory muscles squeezes the outer surface of the lung adding to the positive pressure by further compressing the air in the lung. Again, this is analogous to putting an inflated balloon in your hands and squeezing the balloon.

For example, as shown in FIG. 1, the net positive pressure in the lung is the sum of the elastic recoil pressure and the expiratory muscle squeeze pressure. Thus, if the elastic recoil pressure with an inflated lung is 10 $cmH_2O$ and the expiratory muscles squeeze the lung with 30 $cmH_2O$, the total positive pressure in the alveoli is 40 $cmH_2O$. These pressures are referenced to atmospheric pressure which we consider 0 $cmH_2O$ (i.e., the alveolar pressure is 40 $cmH_2O$ greater than atmospheric pressure). It is also important to recognize that the pressure in the alveoli is 40 $cmH_2O$ and the pressure at the mouth (or nose) is atmospheric or 0 $cmH_2O$. This means that the pressure decreases along the airways going from the alveoli to the mouth with all 40 $cmH_2O$ dissipating along this path. The pressure is lost due to the resistance of the respiratory tract.

Another important feature of the respiratory anatomy is that the lung and all the airways are within the thorax except for approximately half the trachea, the pharynx, and mouth. This means that when the expiratory muscles contract, the squeeze pressure is applied to the entire thoracic cavity, which applies the squeeze pressure equally to the entire lung (alveoli and airways) within the thorax. In our example, that means that 30 $cmH_2O$ squeezing pressure is applied to the alveoli and the intrathoracic airways. The alveoli have a net positive pressure of 40 $cmH_2O$ because of the combination of the elastic recoil pressure and the expiratory muscle squeeze pressure. This results in a greater pressure in the alveoli than outside the alveoli and the alveoli stay distended. As noted above, however, the intra-airway pressure decreases due to loss of pressure from airway resistance. That means the closer to the mouth, the lower the positive pressure inside the airway. At some point in this path, the intra-airway pressure will decrease to 30 $cmH_2O$. This happens in intrathoracic airways. At this point, the pressure inside the airway equals the expiratory muscle squeeze pressure outside the airway and is called the Equal Pressure Point (EPP).

Moving closer to the mouth from the EPP results in a further decrease in the intra-airway pressure. Now, the intra-airway pressure is less than the expiratory muscle squeeze pressure and there is a net collapsing force applied to the airway. As the airway is compressed, the resistance increases and more pressure is lost due to the elevated resistive forces.

The reason peak expiratory airflow during forced expirations is effort independent, is because the greater the expiratory effort, the greater the expiratory muscle squeeze, and the greater the compression force beyond the EPP. This increased airway compression increases the resistance and dissipates more pressure as air flows through the compressed airway. This creates a physical limit to the maximum airflow because no matter how much greater the positive pressure from active expiratory muscle contraction driving force, there is a proportional increase in airway collapse, limiting the airflow, making the peak airflow rate measured at the mouth effort independent.

In the normal lung, the EPP occurs in bronchi that contain cartilage. The cartilage limits the compression of the airway and protects the airway from collapse with forced expirations. With emphysema, as shown in FIG. 2, there is a loss of lung elasticity recoil, meaning, that with inflation of the lung the elastic recoil pressure portion of the positive alveolar pressure is decreased. When the expiratory muscles contract during emphysema, as in the example above, a 30 $cmH_2O$ squeeze pressure is generated. The net alveolar pressure is now 30 $cmH_2O$ squeeze pressure with a reduced elastic recoil pressure, for example 5 $cmH_2O$, making the net alveolar pressure 35 $cmH_2O$. Again, pressure is dissipated as air flows towards the mouth. With this emphysema example, the EPP will occur closer to the alveoli as the intra-airway pressure goes from 35 to 30 $cmH_2O$ quicker than the normal lung which went from 40 to 30 $cmH_2O$. Thus, the EPP moves closer to the alveoli and can even occur in bronchioles which are airways that do not have cartilage.

If the EPP occurs in non-cartilaginous airways, then airway collapse can occur due to the expiratory muscle squeeze pressure being greater than the intra-airway pressure with no cartilage to prevent the collapse of the airway. When the airway collapses, gas is trapped in the lung and the patient cannot fully empty their lung resulting in hyperinflation, called dynamic hyperinflation. In this condition, exhaling with a greater effort provides no relief.

One method used to assist emphysema patients with this type of gas trapping is to use pursed-lips breathing. This requires patients to breathe out through their mouths with the lips partially closed as if they were whistling. This increases the airflow resistance at the mouth creating an elevated pressure behind the lip obstruction, like partially covering a water hose with your thumb which creates a higher pressure behind the obstruction. Pursed-lips breathing increases the pressure down the respiratory tract creating a positive expiratory pressure (PEP) and functionally moves the EPP closer to the mouth. This is an airflow dependent (because it works only when air is moving) method of compensating for dynamic airway collapse in COPD patients. This prevents some of the collapse of the airways and permits additional deflation of the lung, reducing the dynamic hyperinflation.

Increasing the intra-airway pressure during expiration by creating a positive end pressure, PEP, is an important method for maintaining airway patency, decreasing gas trapping and reducing hyperinflation in emphysema patients. Several attempts have been made to manufacture resistance devices which imitate pursed-lips breathing, including U.S. Pat. Nos. 4,523,137 to Sonne; 4,601,465 to Ray; and 5,598,839 to Niles. These devices are successful in producing the same effect as pursed-lips breathing, but only marginally effective in reducing the dynamic hyperinflation in severe COPD. The marginal effectiveness in reducing the dynamic hyperinflation in severe COPD occurs as a result of the method being airflow dependent, meaning, i.e. there is no PEP unless the patient is actually moving air. Thus, when airflow is maximum, the PEP effect is maximum, and the EPP will be moved closer to the mouth. However, most COPD patients cannot generate and sustain high expiratory airflows. In fact, the expiratory airflow pattern is characterized by the peak airflow early in the expiration with a rapidly diminished airflow. As the expiration progresses, airflow tails-off, with very low flows as the expiration ends. This results in very little PEP in the latter half of the expiration which abolishes much of the effect of dynamic hyperinflation reduction.

What is needed is a significant PEP throughout the entire expiration which will keep the airways open allowing them to properly deflate. This would then decrease end-expiratory lung volume, allow for better inspiratory pumping (by making the diaphragm go closer to its optimal contraction length), increase alveolar ventilation, increase the $O_2$ in the blood, decrease the $CO_2$ in the blood, and decrease the sense of breathlessness that causes great distress in these patients.

Most COPD patients live a restricted lifestyle because of severe breathlessness, inability to exercise and need for supplemental oxygen. When queried, most patients are desperate for a solution to reduce their primary distressing symptom, breathlessness. Clinicians need non-pharmacological methods to improve the $O_2$ and $CO_2$ status of the patient and to treat the dynamic hyperinflation. Current use of bronchodilators and resistance breathing methods are helpful but produce only modest improvements in many cases.

BRIEF SUMMARY OF THE INVENTION

The present invention is directed to a breathing method which increases intra-airway pressure in a patient, thus causing a positive expiratory pressure (PEP) which is not airflow dependent. More specifically, the present invention provides methods which utilize a pressure relief valve, preferably a positive end-expiratory pressure (PEEP) valve, for providing positive expiratory pressure (PEP). The PEP is caused by directing the flow of gases exhaled by the patient through the PEEP valve, so that gases must be exhaled against the PEEP valve held closed by threshold pressure. In this way, gases exhaled by the patient are subject to positive exhalation pressure set by the threshold pressure, which in turn increase the pressure in the patient's airway. When the expiratory pressure exceeds the threshold pressure of the valve, the valve opens and air is exhaled.

In accordance with the practice of the present invention, patients breathe out through a PEEP valve, generating enough pressure to overcome the PEEP valve's pressure threshold, allowing air to flow through the PEEP valve. Expiring through the PEEP valve creates a PEP equal to the PEEP valve's pressure. The PEP produced by the PEEP valve results in increased airway patency, such that the amount of gas trapped in the lung decreases (reduced hyperinflation) and the airway resistance decreases.

The elevated PEP from a PEEP valve remains in the airway throughout the expiration, even to the very end, moving the Equal Pressure Point (EPP) closer to the mouth, and keeping it there. The decreased hyperinflation returns the diaphragm closer to its normal length, increasing the ability of the diaphragm to generate the inspiratory pumping forces. Improving the ability of these patients to ventilate their lungs increases their exercise tolerance and decreases their sense of breathlessness.

The novel application of the PEEP valve according to the present invention provides an inexpensive and non-pharmacological method of reducing breathlessness, increasing exercise capacity and improving alveolar ventilation.

All patents, patent applications and publications referred to or cited herein, are incorporated by reference in their entirety to the extent they are not inconsistent with the explicit teachings of this specification.

DETAILED DESCRIPTION OF THE INVENTION

The subject invention provides a method which increases intra-airway pressure in a patient, thus causing a positive expiratory pressure (PEP), which is not airflow dependent. The method of the present invention utilizes a pressure relief valve, preferably a positive end-expiratory pressure (PEEP) valve. The PEP is caused by obstructing the flow of gases exhaled by the patient through the PEEP valve until the PEP is greater than the pressure threshold of the PEEP valve, so that such gases must be exhaled against the PEEP valve's pressure threshold.

Figure 1:
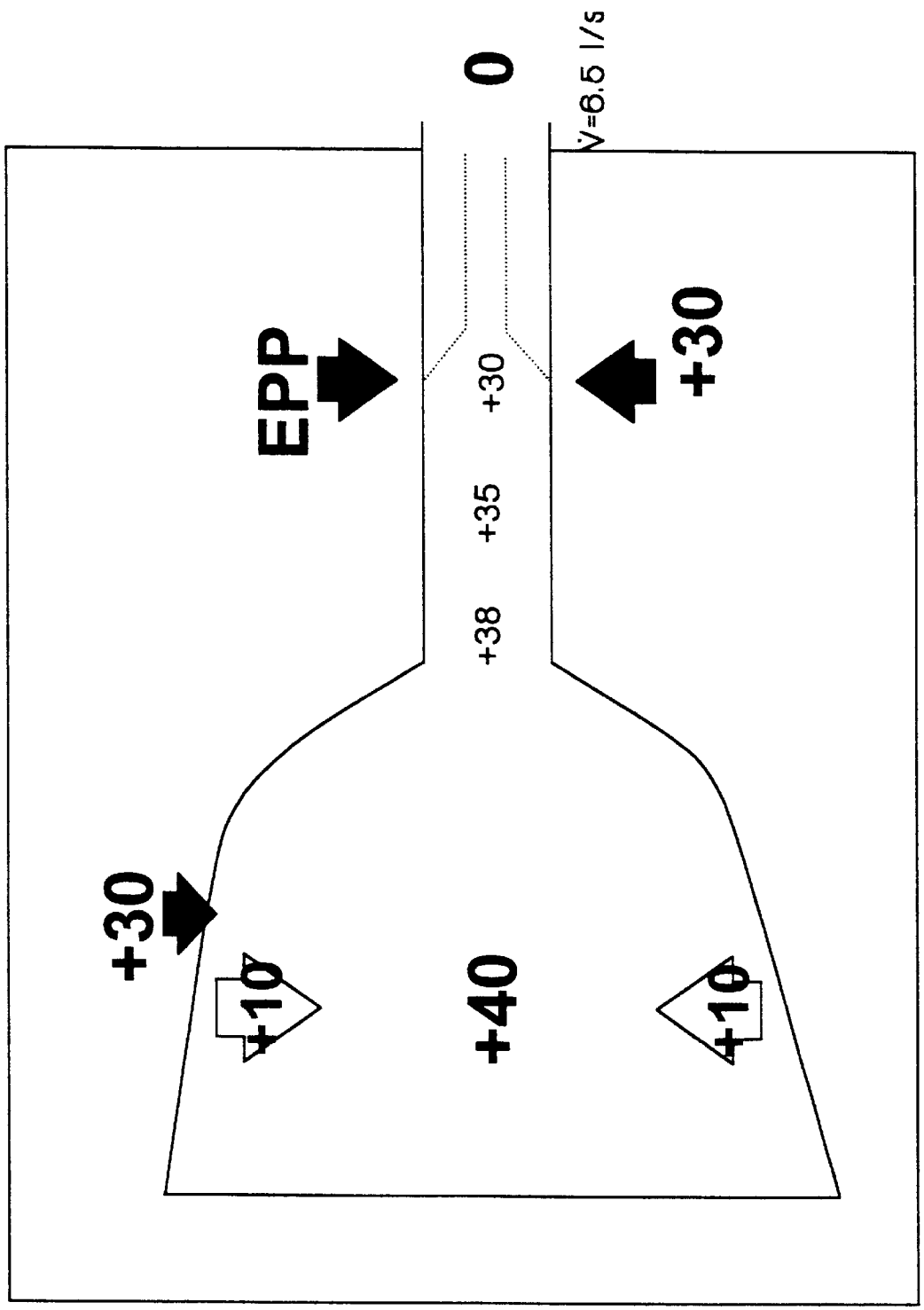
FIG. 1 depicts an example of a patient's health lung exhalation pressure.
Figure 2:
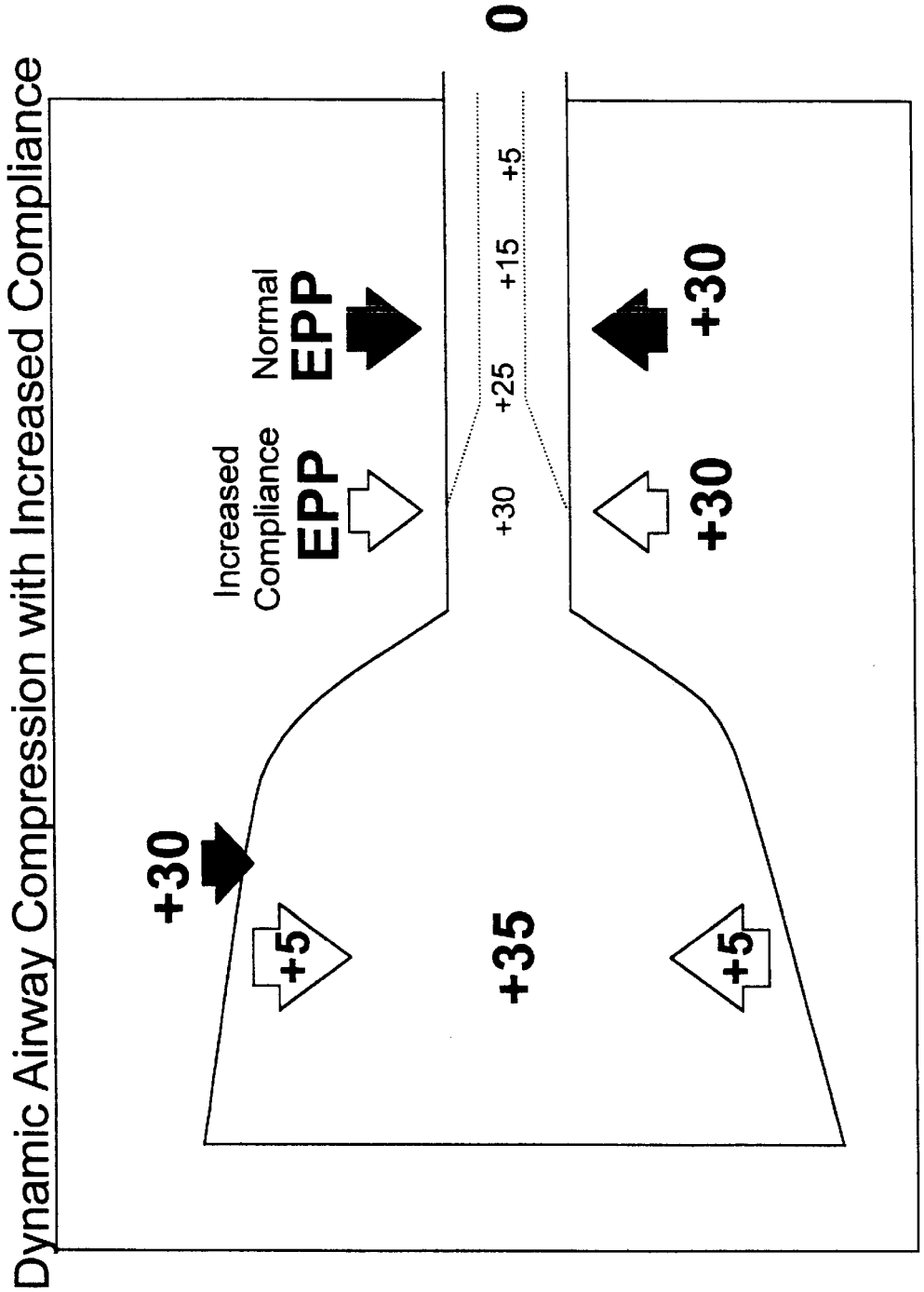
FIG. 2 depicts an example of exhalation pressure for a patient with emphysema.
Figure 3:
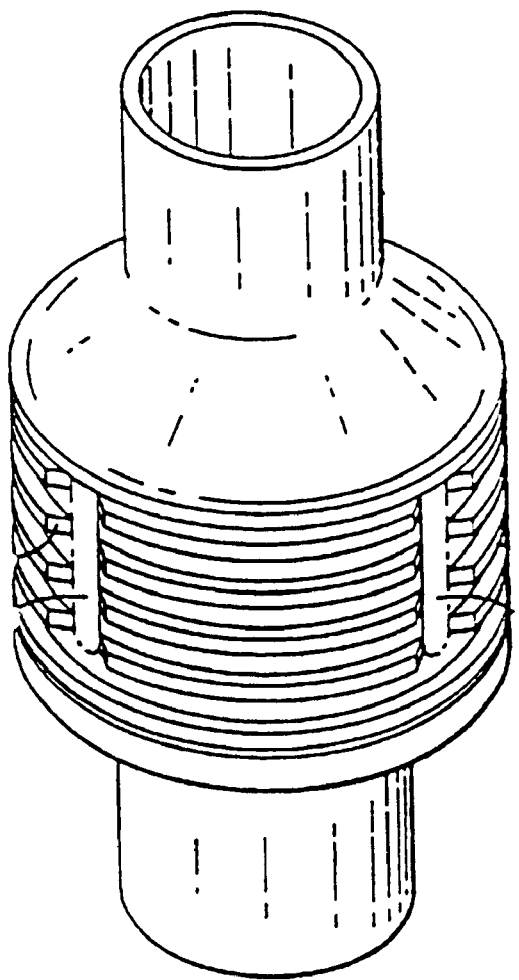
FIG. 3 shows an example of a PEEP valve.

Examples of PEEP valves include, but are not limited to, U.S. Pat. No. 5,878,743 to Zdrojkowski, as shown in FIG. 3, which discloses an unidirectional valve with a spring force to control exhalation pressure; U.S. Pat. No. 1,896,719, to McKesson, discloses a mask having an exhaling valve with a spring force adjustable by a set screw to control exhalation pressure; U.S. Pat. No. 4,182,366, to Boehringer, discloses a spring connected to a diaphragm, whereby the spring urges the diaphragm to close the exhaust port. A thumb screw can be adjusted to control the pressure on the spring; U.S. Pat. No. 4,207,884, to Isaacson, discloses an annular seat on a disk-shaped valve, whereby a spring urges the valve against its seat in accordance with the setting on a graduated plunger. Additional PEEP valves are disclosed in U.S. Pat. Nos. 4,403,616, 4,345,593, 4,870,963, and 5,109,840.

In accordance with the practice of the subject invention the patient breathes out through a valve, generating sufficient pressure to overcome the valve's pressure threshold, allowing air to flow through the valve. Expiring through the valve creates a PEP equal to the valve's pressure threshold. The PEP produced by the valve results in increased airway patency, such that the amount of gas trapped in the lung decreases (reduced hyperinflation) and the airway resistance decreases. The elevated PEP from the valve, equal to the pressure threshold of the valve, remains in the airway throughout the expiration. This decreases end-expiratory lung volume, allows for better inspiratory pumping, increases alveolar ventilation, increases the $O_2$ in the blood, decreases the $CO_2$ in the blood, and decreases the sense of breathlessness that causes great distress in these patients. Also, the decreased hyperinflation returns the diaphragm closer to its normal length, increasing the ability of the diaphragm to generate the inspiratory pumping forces. This improves the ability of the patient to ventilate the lungs, increasing exercise tolerance and decreasing the sense of breathlessness.

In an embodiment of the subject invention, a valve is utilized to increase intra-airway pressure in a patient, thus causing a positive expiratory pressure (PEP) and functionally moving the Equal Pressure Point (EPP) closer to the mouth. The valve is aligned such that the valve's threshold pressure resists the patients exhalation, whereby the threshold pressure is at a level such that the patient is capable of overcoming it upon exhalation through the valve. Initially, the patient inhales, filling the lungs, and then exhales though the valve with sufficient force to overcome the valve's threshold pressure. This inhalation and exhalation is referred to as a breathing cycle.

In an embodiment, the valve comprises a mouth piece, which is placed in the patient's mouth.

In an embodiment, the method of the subject invention is performed while the patient is at rest, or at limited activity. The valve threshold pressure is set to a relatively low threshold pressure level, about 1–5 $cmH_2O$. The patient continually exhales through the valve for a short duration of time, about 2–5 breaths, or about 0.05–1.5 minutes. The method is performed on regular basis, with the valve threshold pressure being increased as the patient's tolerance increases.

In the "at rest" embodiment, to increase the pressure in the patient's intra-airway the valve's threshold pressure is set to about 1–50 cm $H_2O$.

In a specific at rest embodiment, the valve threshold pressure is set to about 10 $cmH_2O$.

In an alternative at rest embodiment, the duration of continual valve usage is increased as the patient's tolerance increases. To increase the pressure in a patient's intra-airway, the patient breathes through the valve continually for about 2–30 breaths.

In an alternative at rest embodiment, the patent continually breathes through the valve for about 0.05 to 30 minutes.

In an alternative method of use, the patient utilizes the valve while performing physical exercise, such as cardiovascular training. The valve threshold pressure is set to a low threshold pressure level, about 1–5 $cmH_2O$. While exercising, the patient continually exhales through the valve. Initially, the patient will exercise for a relatively short duration, about 0.05–5 min. As the patient's tolerance increases, the duration of the exercise increases.

In the "increased activity" embodiment, to increase the pressure in the patient's intra-airway, the pressure threshold of the valve is set to about 1–50 cm $H_2O$.

In a specific increased activity embodiment, the valve threshold pressure is set to about 10 $cmH_2O$.

In an alternative increased activity embodiment, the duration of continual exercise is for about 0.05 to 30 minutes.

It should be understood that the examples and embodiments described herein are for illustrative purposes only and that various modifications or changes in light thereof will be suggested to persons skilled in the art and are to be included within the spirit and purview of this application and claims.

What is claimed is:

1. A method for creating an airflow independent positive expiratory pressure (PEP) in a patient's respiratory system using a pressure relief valve comprising:
   a) selecting a pressure threshold of the pressure relief valve between about 1 $cmH_2O$ and 50 $cmH_2O$ such that the patient can overcome said pressure threshold upon forced exhalation through said pressure relief valve; and
   b) positioning said pressure relief valve in the patient's mouth during exhalation of at least one breathing cycle, such that said pressure threshold resists the patient's exhalation until sufficient force is produced to overcome said pressure threshold.

2. The method for creating an airflow independent positive expiratory pressure in a patient's respiratory system according to claim 1, wherein said pressure threshold is between about 1 $cmH_2O$ and 40 $cmH_2O$.

3. The method for creating an airflow independent positive expiratory pressure in a patient's respiratory system according to claim 1, wherein said pressure threshold is between about 1 $cmH_2O$ and 30 $cmH_2O$.

4. The method for creating an airflow independent positive expiratory pressure in a patient's respiratory system according to claim 1, wherein said pressure threshold is between about 1 $cmH_2O$ and 20 $cmH_2O$.

5. The method for creating an airflow independent positive expiratory pressure in a patient's respiratory system according to claim 1, wherein said pressure threshold is between about 1 $cmH_2O$ and 10 $cmH_2O$.

6. The method for creating an airflow independent positive expiratory pressure in a patient's respiratory system according to claim 1, wherein said pressure threshold is between about 10 $cmH_2O$ and 50 $cmH_2O$.

7. The method for creating an airflow independent positive expiratory pressure in a patient's respiratory system according to claim 1, wherein said pressure threshold is between about 20 $cmH_2O$ and 50 $cmH_2O$.

8. The method for creating an airflow independent positive expiratory pressure in a patient's respiratory system according to claim 1, wherein said pressure threshold is between about 30 $cmH_2O$ and 50 $cmH_2O$.

9. The method for creating an airflow independent positive expiratory pressure in a patient's respiratory system according to claim 1, wherein said pressure threshold is between about 40 $cmH_2O$ and 50 $cmH_2O$.

10. The method for creating an airflow independent positive expiratory pressure in a patient's respiratory system according to claim 1, wherein said pressure threshold is between about 5 $cmH_2O$ and 15 $cmH_2O$.

11. The method for creating an airflow independent positive expiratory pressure in a patient's respiratory system according to claim 1, wherein said pressure threshold is between about 1 $cmH_2O$ and 5 $cmH_2O$.

12. The method for creating an airflow independent positive expiratory pressure in a patient's respiratory system according to claim 1, wherein said pressure threshold is about 10 cmH$_2$O.

13. The method for creating an airflow independent positive expiratory pressure in a patient's respiratory system according to claim 1 wherein the pressure relief valve is positioned throughout a plurality of breathing cycles.

14. The method for creating an airflow in dependent positive expiratory pressure in a patient's respiratory system according to claim 13, wherein the duration of the plurality of breathing cycles is about 0.05 minutes to 30 minutes.

15. The method for creating an airflow in dependent positive expiratory pressure in a patient's respiratory system according to claim 13, wherein the duration of the plurality of breathing cycles is about 5 minutes to 30 minutes.

16. The method for creating an airflow in dependent positive expiratory pressure in a patient's respiratory system according to claim 13, wherein the duration of the plurality of breathing cycles is about 10 minutes to 30 minutes.

17. The method for creating an airflow in dependent positive expiratory pressure in a patient's respiratory system according to claim 13, wherein the duration of the plurality of breathing cycles is about 20 minutes to 30 minutes.

18. The method for creating an airflow in dependent positive expiratory pressure in a patient's respiratory system according to claim 13, wherein the duration of the plurality of breathing cycles is about 0.05 minutes to 20 minutes.

19. The method for creating an airflow in dependent positive expiratory pressure in a patient's respiratory system according to claim 13, wherein the duration of the plurality of breathing cycles is about 0.05 minutes to 10 minutes.

20. The method for creating an airflow in dependent positive expiratory pressure in a patient's respiratory system according to claim 1, wherein the duration of the plurality of breathing cycles is about 0.05 minutes to 5 minutes.

21. The method for creating an airflow in dependent positive expiratory pressure in a patient's respiratory system according to claim 13, wherein the duration of the plurality of breathing cycles is about for about 0.05 minutes to 1.5 minutes.

22. The method for creating an airflow independent positive expiratory pressure in a patient's respiratory system according to claim 13, wherein the breathing cycles comprises about 2 to 30 exhalations.

23. The method for creating an airflow independent positive expiratory pressure in a patient's respiratory system according to claim 13, wherein the breathing cycles comprises about 10 to 20 exhalations.

24. The method for creating an airflow independent positive expiratory pressure in a patient's respiratory system according to claim 13, wherein the breathing cycles comprises about 2 to 20 exhalations.

25. The method for creating an airflow independent positive expiratory pressure in a patient's respiratory system according to claim 13, wherein the breathing cycles comprises about 2 to 10 exhalations.

26. The method for creating an airflow independent positive expiratory pressure in a patient's respiratory system according to claim 13, wherein the breathing cycles comprises about 10 to 30 exhalations.

27. The method for creating an airflow independent positive expiratory pressure in a patient's respiratory system according to claim 13, wherein the breathing cycles comprises about 20 to 30 exhalations.

28. The method for creating an airflow independent positive expiratory pressure in a patient's respiratory system according to claim 1, wherein said pressure relief valve is a positive end-expiratory pressure valve.

29. The method for creating an airflow independent positive expiratory pressure in a patient's respiratory system according to claim 1, wherein the patient inhales through said pressure relief valve and exhales through said pressure relief valve.

30. A respiratory exercise method for creating an airflow independent positive expiratory pressure (PEP) in a patient's respiratory system using a pressure relief valve comprising:
   a) selecting a pressure threshold of the pressure relief valve between about 1 cmH$_2$O and 50 cmH$_2$O such that the patient can overcome said pressure threshold upon forced exhalation through said pressure relief valve; and
   b) positioning said pressure relief valve in the patient's mouth during exhalation while exercising for about 0.05 minutes to 30 minutes, such that said pressure threshold resists the patient's exhalation until sufficient force is produced to overcome said pressure threshold.

31. A method for increasing the intra-airway pressure in a patient's respiratory system comprising:
   a) selecting a means for creating a positive expiratory pressure in the patient's respiratory system; and
   b) positioning said means for creating a positive expiratory pressure in the patient's mouth during exhalation while exercising for about 0.05 minutes to 30 minutes, such that said pressure threshold resists the patient's exhalation until sufficient force is produced to overcome said pressure threshold.

* * * * *